(12) United States Patent
Lanza di Scalea

(10) Patent No.: US 9,950,715 B2
(45) Date of Patent: Apr. 24, 2018

(54) AIR-COUPLED ULTRASONIC INSPECTION OF RAILS

(71) Applicant: The Regents of the University of California, Oakland, CA (US)

(72) Inventor: Francesco Lanza di Scalea, San Diego, CA (US)

(73) Assignee: The Regents Of The University Of California, Oakland, CA (US)

( * ) Notice: Subject to any disclaimer, the term of this patent is extended or adjusted under 35 U.S.C. 154(b) by 438 days.

(21) Appl. No.: 14/389,052

(22) PCT Filed: Apr. 2, 2013

(86) PCT No.: PCT/US2013/034977
§ 371 (c)(1),
(2) Date: Sep. 29, 2014

(87) PCT Pub. No.: WO2013/152018
PCT Pub. Date: Oct. 10, 2013

(65) Prior Publication Data
US 2015/0068296 A1    Mar. 12, 2015

Related U.S. Application Data

(60) Provisional application No. 61/621,342, filed on Apr. 6, 2012.

(51) Int. Cl.
*G01N 29/24* (2006.01)
*B61K 9/00* (2006.01)
(Continued)

(52) U.S. Cl.
CPC .................. *B61K 9/00* (2013.01); *B06B 1/02* (2013.01); *B60T 17/18* (2013.01); *B61K 9/10* (2013.01);
(Continued)

(58) Field of Classification Search
CPC .. B06B 1/02; B60T 17/18; B61K 9/00; B61K 9/10; G01B 17/00; G01B 17/04;
(Continued)

(56) References Cited

U.S. PATENT DOCUMENTS 5,777,891 A * 7/1998 Pagano .............. G01N 29/0609
702/39
6,055,862 A * 5/2000 Martens ............. G01N 29/2493
73/632

(Continued)

FOREIGN PATENT DOCUMENTS

WO    WO 2010036934 A2 * 4/2010 ........... G01N 29/043

OTHER PUBLICATIONS

International Search Report dated Jul. 18, 2013, for PCT application No. PCT/US2013/034977.

*Primary Examiner* — Freddie Kirkland, III
(74) *Attorney, Agent, or Firm* — Mintz Levin Cohn Ferris Glovsky and Popeo, P.C.

(57) ABSTRACT

In some example implementations, there is provided a method. The method may include generating, by an air-coupled transducer, a first ultrasonic guided wave to cause the generated ultrasonic guided wave to propagate into a rail being tested for one or more defects, wherein a frequency of the first ultrasonic guided wave is controlled by at least changing the frequency of a voltage sent to the air-coupled transducer generating the first ultrasonic guided wave; receiving, by a receiver, a second ultrasonic guided wave, wherein the second ultrasonic guided wave is received from the rail; and analyzing a signal representative of the received second ultrasonic guided wave to detect the one or more defects in the rail. Related systems, methods, and articles of manufacture are also provided.

20 Claims, 11 Drawing Sheets

(51) Int. Cl.
*B61K 9/10* (2006.01)
*G01B 17/04* (2006.01)
*G01N 29/12* (2006.01)
*G01N 29/44* (2006.01)
*G01N 29/46* (2006.01)
*G01B 17/00* (2006.01)
*B06B 1/02* (2006.01)
*B60T 17/18* (2006.01)
*G01D 5/12* (2006.01)
*G01N 29/04* (2006.01)

(52) U.S. Cl.
CPC ............ *G01B 17/00* (2013.01); *G01B 17/04* (2013.01); *G01D 5/12* (2013.01); *G01N 29/04* (2013.01); *G01N 29/12* (2013.01); *G01N 29/2462* (2013.01); *G01N 29/4436* (2013.01); *G01N 29/46* (2013.01); *G01N 2291/0425* (2013.01); *G01N 2291/2623* (2013.01)

(58) Field of Classification Search
CPC ............. G01D 5/12; G01N 2291/0425; G01N 2291/2623; G01N 29/04; G01N 29/12; G01N 29/2462; G01N 29/4436; G01N 29/46
See application file for complete search history.

(56) References Cited

U.S. PATENT DOCUMENTS

| | | | |
|---|---|---|---|
| 6,186,004 B1 * | 2/2001 | Kaduchak | G01N 29/036 73/596 |
| 6,324,912 B1 * | 12/2001 | Wooh | B61K 9/10 73/629 |
| 6,401,044 B1 * | 6/2002 | Ibanez Rodriguez | B61K 9/12 702/34 |
| 6,715,354 B2 * | 4/2004 | Wooh | B61K 9/10 73/598 |
| 7,882,742 B1 * | 2/2011 | Martens | G01N 29/07 73/632 |
| 7,942,058 B2 * | 5/2011 | Turner | B61K 9/08 73/602 |
| 8,020,446 B2 * | 9/2011 | Bestebreurtje | G01N 29/043 73/627 |
| 8,176,786 B2 * | 5/2012 | Sohn | G01N 29/069 73/598 |
| 8,626,459 B2 * | 1/2014 | Di Scalea | G01N 29/043 702/34 |
| 9,010,186 B2 * | 4/2015 | Pagano | G01N 29/04 73/636 |
| 2004/0003662 A1 * | 1/2004 | Kenderian | G01N 29/12 73/579 |
| 2006/0201253 A1 * | 9/2006 | Gonzales | G01N 29/0618 73/643 |
| 2008/0223137 A1 * | 9/2008 | Bestebreurtje | G01N 29/043 73/628 |
| 2009/0056454 A1 * | 3/2009 | Turner | B61K 9/08 73/600 |
| 2009/0301198 A1 * | 12/2009 | Sohn | G01N 29/069 73/598 |
| 2010/0024559 A1 | 2/2010 | Bossi et al. | |
| 2011/0238336 A1 * | 9/2011 | Di Scalea | G01N 29/043 702/56 |
| 2016/0304104 A1 * | 10/2016 | Witte | G01N 29/07 |
| 2016/0305915 A1 * | 10/2016 | Witte | G01N 29/07 |

* cited by examiner

AIR-COUPLED ULTRASONIC INSPECTION OF RAILS

RELATED APPLICATION

This application is a national stage application, filed under 35 U.S.C. § 371, of PCT Application No. PCT/US2013/034977, filed on Apr. 2, 2013, and claims priority to U.S. Provisional Application No. 61/621,342, filed on Apr. 6, 2012, the contents of both of which are incorporated herein by reference in its entirety.

STATEMENT OF GOVERNMENT SPONSORED SUPPORT

This invention was made with government support under grant No. FR-RRD-0027-10-11-01-00 awarded by Federal Railroad Administration. The government has certain rights in the invention.

CROSS-REFERENCE TO RELATED APPLICATION

This application claims priority under 35 U.S.C. § 119(e) to U.S. Provisional Patent Application No. 61/621,342, filed on Apr. 6, 2012, the disclosure of which is incorporated herein by reference in its entirety.

BACKGROUND

Today, rail is inspected regularly for defects, such as cracks and the like, many of which are internal to the rail. If undetected, some defects can worsen over time and lead to catastrophic accidents, such as train derailments. To avoid such catastrophes, the regular inspection of rail is mandated by many jurisdictions.

SUMMARY

Methods and apparatus, including computer program products, are provided for using non-contact transducers located at a distance from the rail surface to inspect rails ultrasonically and without physical contact with it.

In some implementations, there may be provided a method. The method may include generating, by an air-coupled transducer, a first ultrasonic guided wave to cause the generated ultrasonic guided wave to propagate into a rail being tested for one or more defects, wherein a frequency of the first ultrasonic guided wave is controlled by at least changing the frequency of a voltage sent to the air-coupled transducer generating the first ultrasonic guided wave; receiving, by a receiver, a second ultrasonic guided wave, wherein the second ultrasonic guided wave is received from the rail; and analyzing a signal representative of the received second ultrasonic guided wave to detect the one or more defects in the rail.

In some implementations, there may also be provided an apparatus. The apparatus may include a first air-coupled ultrasonic transducer configured to generate a first ultrasonic guided wave and to cause the generated ultrasonic guided wave to propagate into a rail being tested for one or more defects; a controller configured to control the frequency of the first ultrasonic guided wave by at least changing a frequency of a voltage sent to the air-coupled transducer generating the first ultrasonic guided wave; a receiver configured to receive a second ultrasonic guided wave, the second ultrasonic guided wave received from the rail being tested for defects; and a processor configured to analyze a signal representative of the received second ultrasonic guided wave to detect the one or more defects in the rail.

In some implementations, one of more variations may be made as well as described in the detailed description below and/or as described in the following features. The air-coupled transducer may include the receiver configured to receive the second ultrasonic guided wave. The receiver may include a plurality of receivers. The receiver may include at least one wheel containing at least one transducer configured to receive the second ultrasonic guided wave. The air-coupled transducer and the receiver may be configured in at least one of a mono-directional inspection mode or a bi-directional inspection mode. The generated first ultrasonic guided wave may include at least one of a rectangular shape or a circular shape, when measured at a surface of the rail. The at least one of the rectangular shape or the circular shape may be at least one of focused or unfocused with respect to the surface of the rail. The air-coupled transducer may include one or more of a piezoelectric crystal, a piezo-composite crystal, or a capacitive device. The analyzing may include comparing a signal representative of the second ultrasonic guided wave to a reference signal and then determining, based on the comparing, whether a defect is present in the rail. The analyzing may include processing a signal representative of the second ultrasonic guided wave, wherein the processing includes matched filtering based on an excitation signal of a controlled frequency. The analyzing may include processing a signal representative of the second ultrasonic guided wave, wherein the processing includes statistically processing the signal based on at least one of following: an outlier analysis, an anomaly detection, or a discordancy test, wherein the statistical processing enables a comparison of a current measurement to a set of historical reference measurements of the rail.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

BRIEF DESCRIPTION OF THE DRAWING

These and other aspects will now be described in detail with reference to the following drawings.

Like reference symbols in the various drawings indicate like elements.

DETAILED DESCRIPTION

The subject matter disclosed herein relates to apparatus and methods for inspecting rail to identify defects in the rail by using at least one air-coupled transducer configured to generator and/or a detect ultrasonic waves used to detect one or more defects in rails, without the transducer making contact with the rail. The air-coupled transducers are configured to not make contact (e.g., touch) the rail's surface. Rather, the air-coupled transducers are located at a standoff distance from the surface of the rail for non-contact testing. This distance may be approximately 0.125 inches or more, although other distances may be used as well. The air-coupled transducer configured to generate the ultrasonic waves may also be referred to as a transducer, an ultrasonic transducer, a generator, a transmitter (T), a transmitting transducer, and a crystal transducer, and the air-coupled detector that receives the ultrasonic waves from rail may be referred to as a receiver (R), a detector, a receiving transducer, and a crystal transducer.

The phrase ultrasonic guided wave refers to a wave in the ultrasonic portion of the spectrum that propagates between or along boundaries of the rail object. The ultrasonic guided waves may additionally include one or more of the following types of waves: Lamb waves, Stoneley waves, Rayleigh waves, Sezawa waves, and Love waves. The detected signal representative of the ultrasonic guided wave may then be processed to determine whether there are any defects in the rail under test. This processing may include a matched filtering to digitally increase the signal-to-noise ratio of the measurements, and/or a statistical analysis to detect the defects, wherein the statistical processing includes one or more of the following: an outlier analysis, an anomaly detection, or a discordancy test.

Generally, rail inspection may be used to detect rail defects, some of which can lead to catastrophic train derailments. The defects may manifest themselves as any type of imperfection in the rail. Examples types of defects include a compound fracture, a gage corner defect, a transverse defect (e.g., a detailed fracture or a transverse fissure), a vertical split head rail, and/or any other type of imperfection that may cause a failure in the integrity of the rail.

Figure 1:
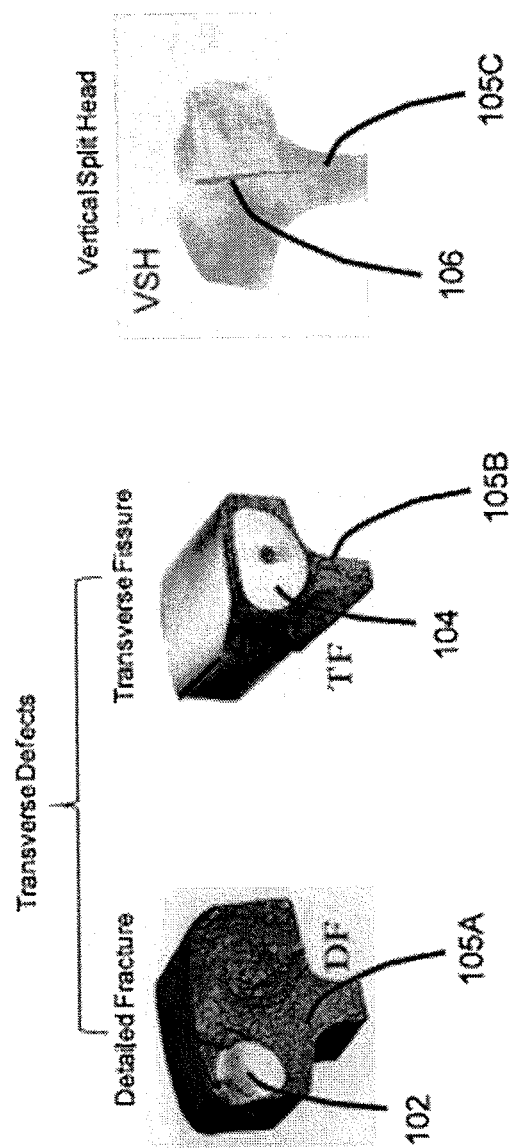
FIG. 1 depicts some examples of defects found in rail.

FIG. 1 depicts examples of defects that can be detected in rail by the systems and methods disclosed herein. Referring to FIG. 1, a rail 105A is shown with a detailed fracture 102, another rail 105B is shown with a transverse fissure 104, and another rail 105C is shown with a vertical split head defect 106. Although FIG. 1 depicts three different types of defects, any other type of imperfection that may cause a failure in the integrity of the rail may be detected as well.

To avoid accidents, such as derailments, the air-coupled ultrasonic guided wave generators and ultrasonic guided wave detectors disclosed herein may be used to inspect rails to detect defects in rail. Moreover, the detection may, in some implementations, be performed as part of targeted, regular maintenance for passenger and freight rails as required by many jurisdictions.

In some implementations, a rail inspection system may include one or more air-coupled transducers. The air-coupled transducer generates and transmits ultrasonic guided waves in the rail, and the detector receives (e.g., detects) the ultrasonic guided waves. The detected ultrasonic guided waves may propagate between, along the boundaries of the rail, and/or substantially parallel to (e.g., in the running direction of) the rail. For example, the wave front associated with the ultrasonic guided wave may propagate in the rail (e.g., in the railhead and the like) in a direction that is in the running direction(s) of the rail, as depicted at 254 at FIG. 2A (which is further described below). The use of ultrasonic guided waves may provide, in some implementations, enhanced detection of defects, when compared to other detection techniques that may miss defects in the rail. As noted, ultrasonic guided waves refer to waves in the ultrasound portion of the spectrum that propagate between or along the boundaries of the rail, and these may include one or more of the following types of waves: Lamb waves, Stoneley waves, Rayleigh waves, Sezawa waves, and Love waves.

Figure 2A:
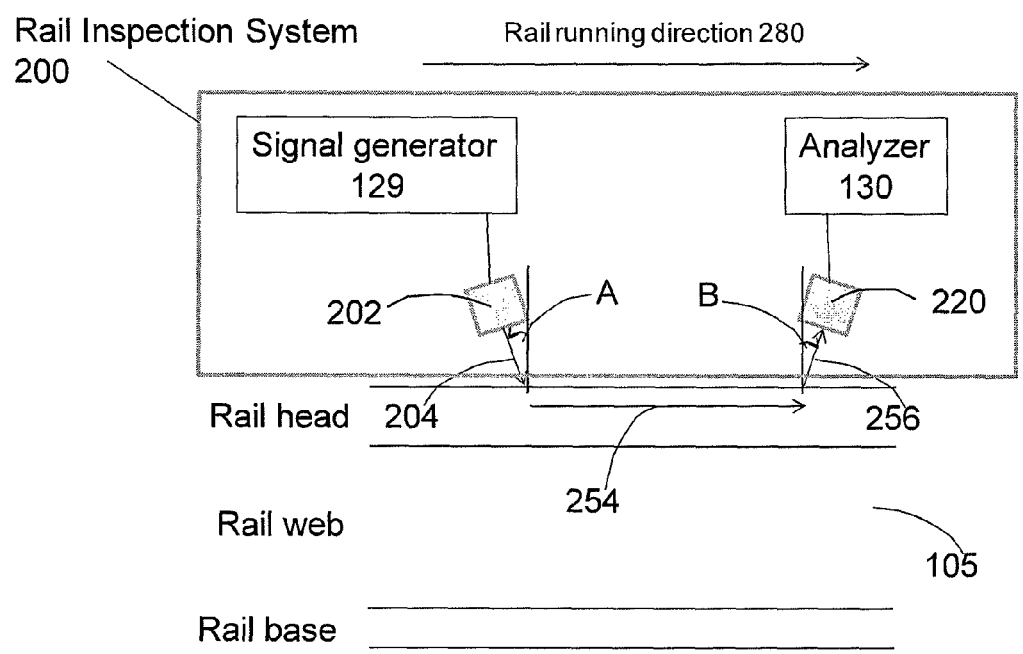
FIGS. 2A, 2B, and 2C depict examples of air-coupled transducers for inspecting rail.

FIG. 2A depicts an example implementation of a rail inspection system 200 configured to travel on rails, such as rail 105 in a running direction 280, in parallel to the rails. Although FIG. 2A depicts a single rail 105, a plurality of rails including parallel rails may be tested by rail inspection system 200 as well, for example monorails, bi-rails, and the like.

The rail inspection system 200 may include at least one air-coupled ultrasonic transducer 202, an analyzer 130, and at least a second air-coupled transducer 220. The air-coupled transducers can be positioned at a distance from the object of approximately 0.125 inch or more, although other distances may be used as well. As the first and second transducers 202, 220 move along the rail running direction, the ultrasonic guided waves 254 are generated and transmitted into rail 105 and detected at transducer 220 to identify defects in the rail 105 under test. Although FIG. 2A depicts two transducers 202 and 220, other quantities of these components may be included in the rail inspection system 200 as well. For example, a plurality of air-coupled generators and a plurality of air-coupled detectors can be utilized in array configurations. Additionally, the detector may be an ultrasonic wheel detector (e.g., hosting one or a plurality of piezoelectric transducers), or a single air-coupled transducer can operate both as a generator and a detector (e.g., pulse-echo testing mode as shown in FIG. 2C described below).

The air-coupled ultrasonic transducers 202 and 220 in FIG. 2A may be piezoelectric crystals, piezo-composite crystals, or capacitive transducers, and these transducers may be able to transmit and/or receive ultrasonic waves to/from air.

The air-coupled ultrasonic transducers 202 and 220 in FIG. 2A may be focused transducers to generate and detect ultrasonic waves focused on a specific portion of the rail surface, for example on a rectangular focus (e.g. a line) or on a circular focus (e.g. a point), although unfocused waves may be used as well.

To illustrate by way of an example and referring again to FIG. 2A, as the rail inspection system 200 travels along rail 105, the generator 202 transmits an ultrasonic wave that travels through air 204 and into rail 105 as ultrasonic guided wave 254. The air-coupled detector 220 receives at 256 the ultrasonic wave through air, which has traveled through rail 105 as ultrasonic guided wave 254. The analyzer 130 may then process signals representative of the received ultrasonic waves to detect whether the received ultrasonic wave encountered any defects in the rail 105. For example, the analyzer 130 may be configured to detect in the received ultrasonic wave any changes in amplitude (and/or energy, phase, velocity and the like) induced by defects, such as cracks and the like, in rail 105. When a defect is detected in rail 105, analyzer 130 may provide an indication of the defect to another processor (e.g., by sending an email or message for presentation at a user interface, and the like). The analyzer 130 may also process signals representative of the detected (or received) ultrasonic guided waves using numerical and/or statistical techniques to detect defects and/or minimize false positive indications, as described further below.

Figure 2B:
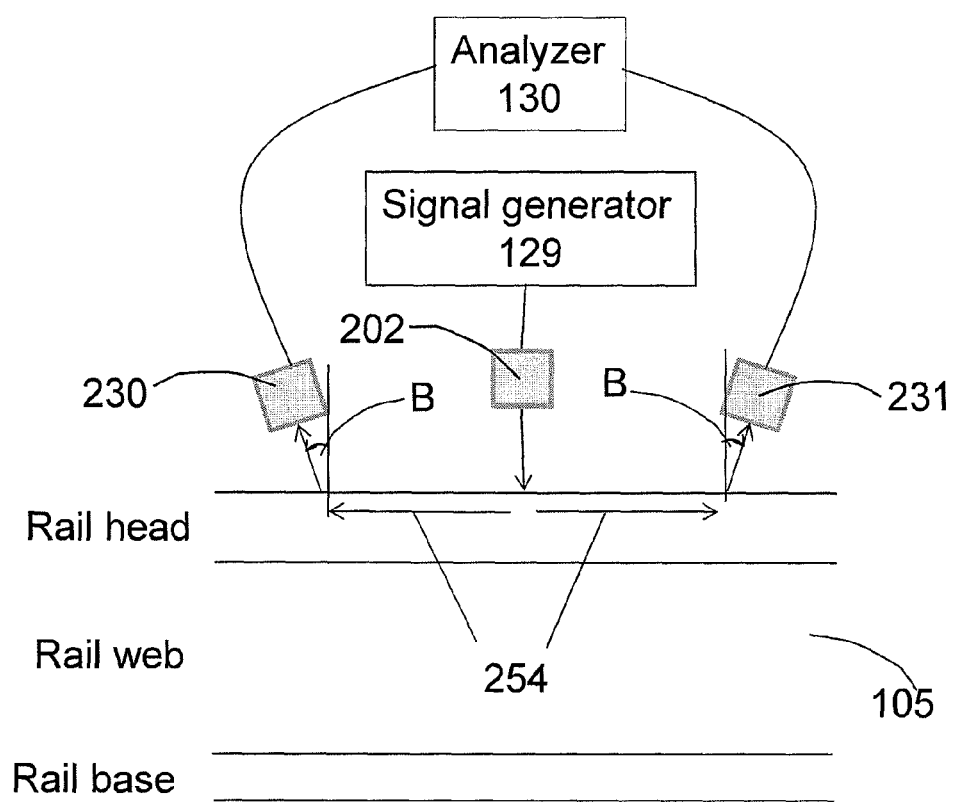
Figure 2C:
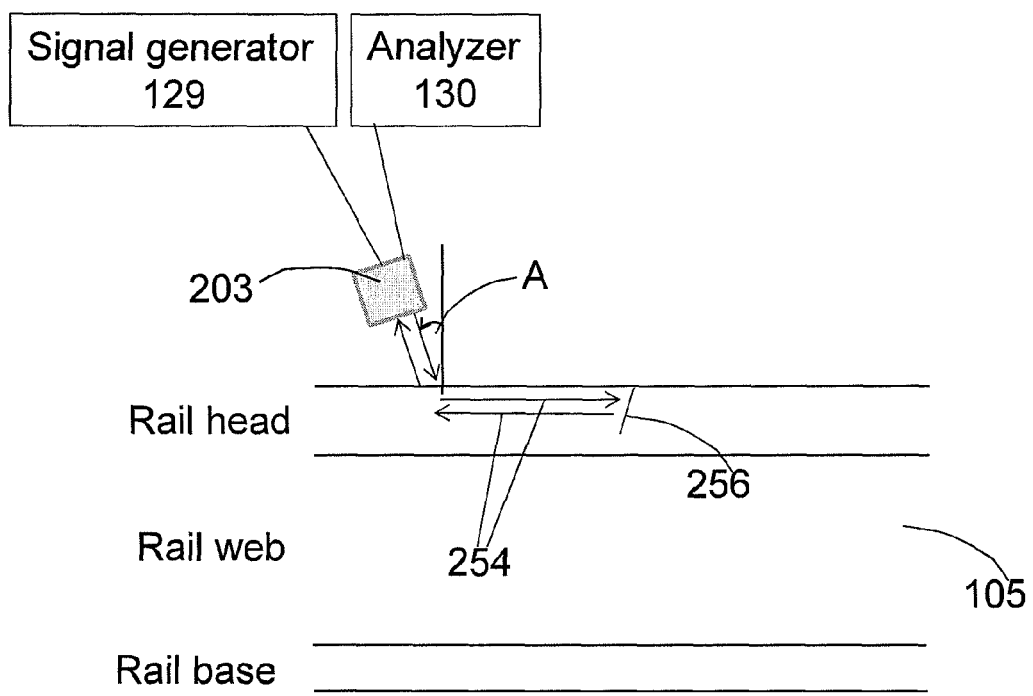

In some implementations, rail inspection system 200 is configured to provide bi-directional mode testing of rail 105 as shown in FIG. 2B. In the bi-directional mode, there are at least two air-coupled detectors, 230 and 231 in FIG. 2B, positioned on opposite sides from the air-coupled generator 202 in FIG. 2B. Air-coupled generator 202 transmits ultrasonic guided wave 254 in both directions into the rail 105, and receivers 230 and 231 detect the ultrasonic guided wave 254. If no defect is present in the rail between the two detectors 230 and 231, the two detectors may measure approximately the same strength of the guided wave. If, instead, a defect is present between the two detectors, the detectors may measure substantially different guided wave signals due to the interaction of the wave with the defect. Therefore, a comparison (e.g., in amplitude, energy, phase, velocity and the like) between the signals measured by the two detectors 230 and 231 may indicate the presence of a defect. The signal comparison can be also done statistically. And, the bi-directional inspection mode may, in some implementations, provide enhanced defect detection in rail 105, when compared to a mono-directional testing using only a single generator and a single receiver as shown in FIG. 2A.

In some implementations, the rail inspection system 200 may travel relatively large distances to perform in-rail testing at speeds up to 30 miles per hour, although other speeds may be used to inspect rails using rail inspection system 200. In some implementations, the air-coupled generator 202 and the air-coupled detector 220 of FIG. 2A may be spaced about 4 inches apart, although other distances may be used as well. In the bi-directional mode, the two air-coupled detectors 230 and 231 of FIG. 2B may be spaced about 8 inches apart, although other distances may be used as well. The rail inspection system 200 may, in some implementations, be configured as at least one air-coupled transducer mounted to a carriage propelled by a vehicle, such as a hyrailer, truck, or train, traveling along rail 105 and the like.

In some implementations, referring to FIG. 2C, the rail inspection system 200 is configured to use a single air-coupled transducer, 203 in FIG. 2C, as a generator and a detector of ultrasonic guided waves in the rail and may be configured in a pulse-echo inspection mode. In this case, the transmitter 203 generates through air an ultrasonic guided wave 254 that is reflected by a defect 256 and detected back at the same transducer 203. The pulse-echo inspection mode refers to a mode where the same transducer acts as an ultrasound generator and as an ultrasound detector.

Figure 3A:
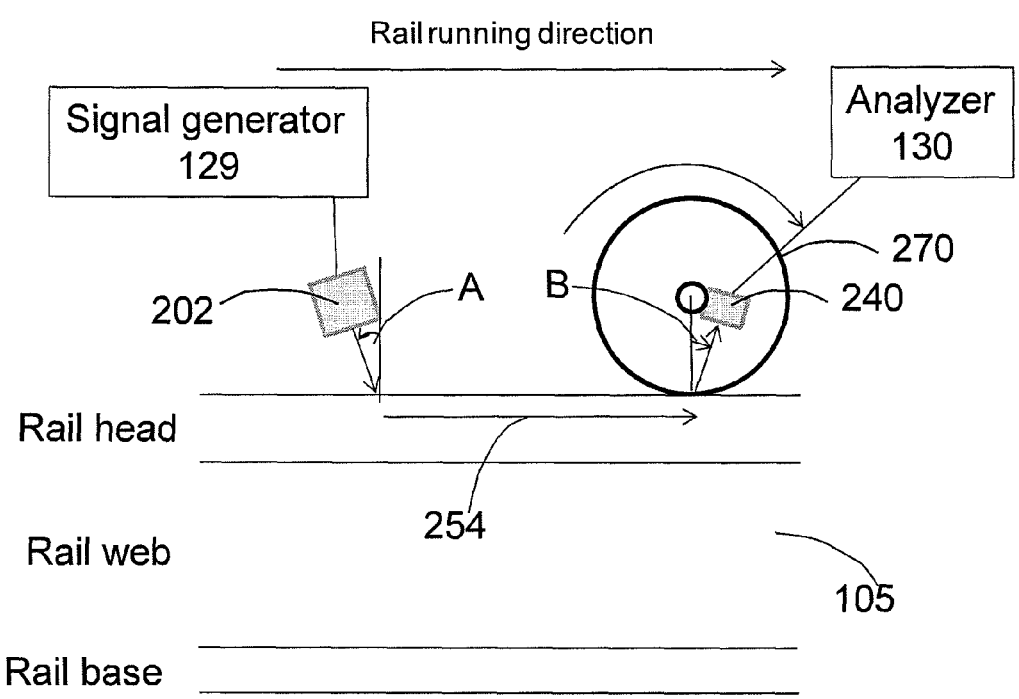
FIGS. 3A and 3B depict examples of hybrid combinations of air-coupled transducers and wheel transducers for inspecting rails.
Figure 3B:
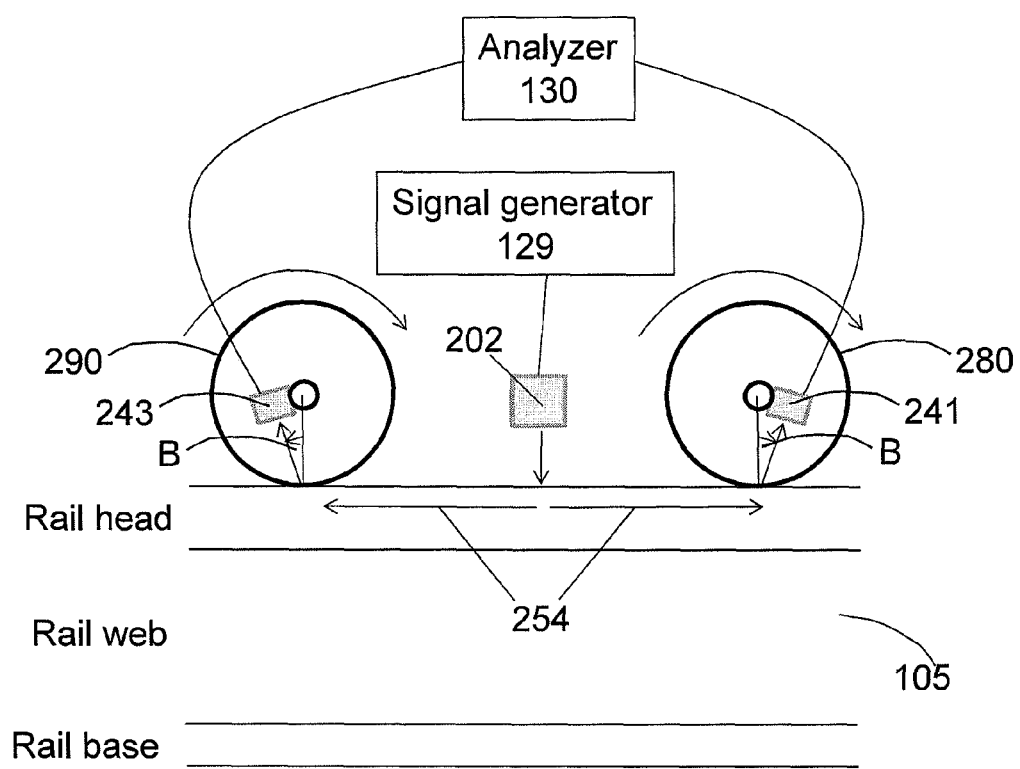

In some implementations, the air-coupled receivers may be replaced by ultrasonic wheels following the configurations shown in FIG. 3A and FIG. 3B, for the mono-directional inspection and the bi-directional inspection, respectively. Therefore, FIG. 3A and FIG. 3B are respectively analogous to FIG. 2A and FIG. 2B, with the difference that the air-coupled receivers 220, 230 and 231 are replaced by the ultrasonic wheel receivers 240, 241 and 243. The ultrasonic wheel receivers consist of piezoelectric transducers 240, 241, 243, that are hosted within fluid-filled wheels 270, 280, 290 that roll over the surface of the railhead. Detecting the ultrasonic guided wave 254 in the rail 105 by the wheels may provide a high signal-to-noise ratio. The piezoelectric transducers inside the wheels can be oriented at specific angles to preferably detect the ultrasonic guided waves according to Snell's law.

In some implementations, the air-coupled generator, such as generator 202, may be oriented such that the ultrasonic guided wave is induced into the rail at an angle A as shown in FIG. 2A. Moreover, this angle A may be configured to be substantially zero, so that the ultrasonic guided wave is induced substantially perpendicularly into the top surface of rail 105 as shown at FIG. 2B. When this is the case, the generator 202 may be configured to aim down straight into the rail 105. In some implementations, the angle A may be different from zero as determined from Snell's law of refraction. In some implementations, the detector, such as detectors 220, 230, 231, may be oriented such that the ultrasonic guided wave is detected from the rail at an angle B that may be configured to comply with Snell's Law of refraction.

Figure 4A:
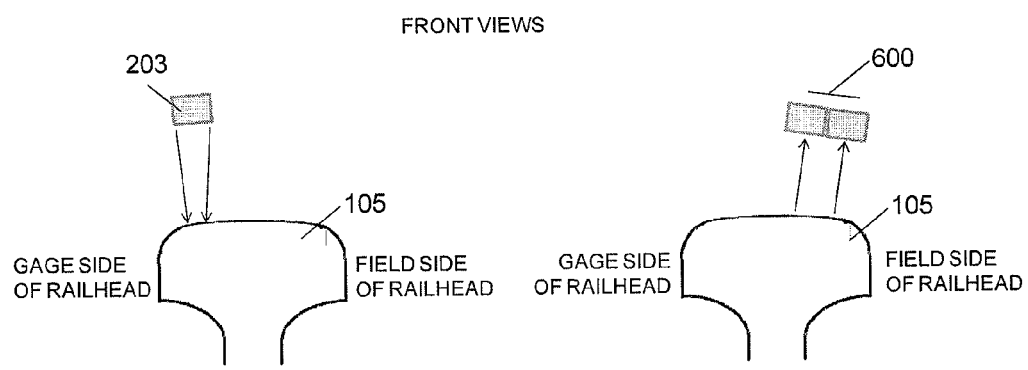
FIGS. 4A, 4B, and 4C depict examples of positions and focii of air-coupled transducers for inspecting rails.
Figure 4B:
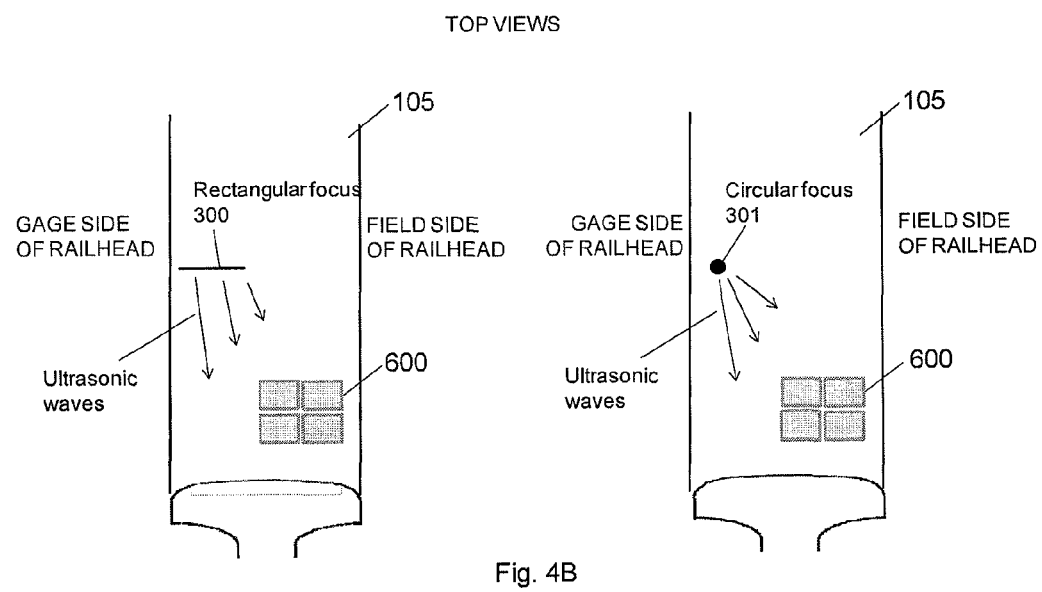
Figure 4C:
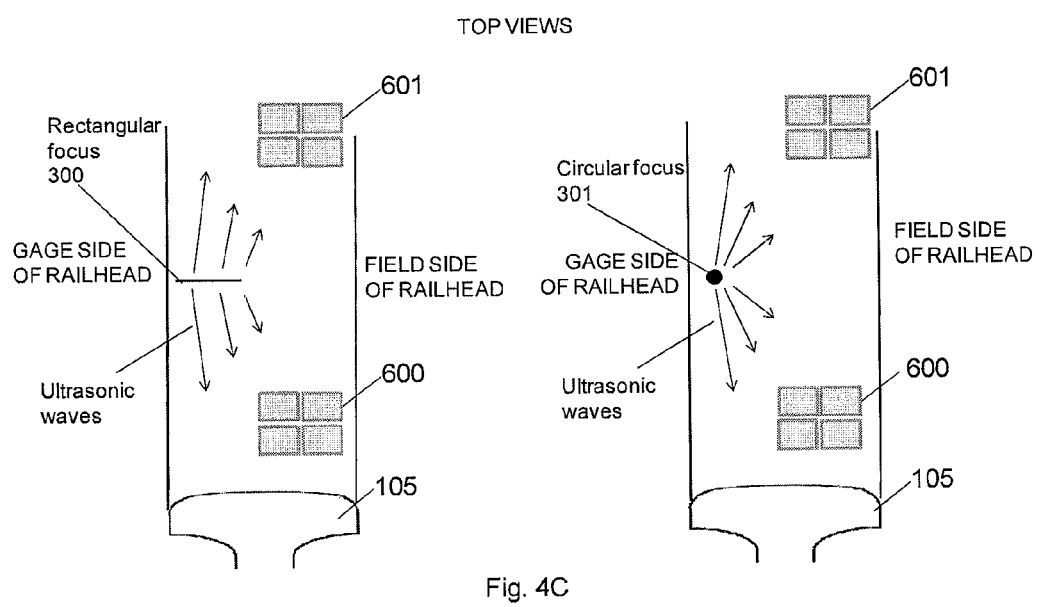

The generators, such as generator 203 in FIG. 4A, may generate an ultrasonic guided wave focused on rail 105 as shown in FIGS. 4A, 4B and 4C. This can be achieved by using a focused transducer or, alternatively, an acoustic lens interposed between the transducer and the rail. The ultrasonic guided wave is focused in the sense that the ultrasonic beam generated through air by the face of the transducer may have a specific shape and a concentrated energy density when it reaches the top of the rail 105. This shape may be a rectangular shape (e.g., a line) 300 in FIGS. 4B and 4C, positioned close to the gage side of the railhead and perpendicular to the rail running direction. In other implementations, the focused shape may be a circular shape (e.g., a point) 301. In FIGS. 4B and 4C, the circular shape is also positioned close to the gage side of the railhead. Both the rectangular focus and the circular focus may generate ultrasonic guided waves that can be received by the at least one air-coupled receiver or by the at least one ultrasonic wheel transducer located close to the field side of the railhead as shown in FIGS. 4A, 4B, and 4C. This so-called "skewed" arrangement (in which the guided wave in the rail is generated close to the gage side and it is detected close to the field side, see, e.g., FIGS. 4A, 4B, and 4C) allows detection of both transverse rail defects (e.g., defects oriented predominantly perpendicularly to the rail's running direction, such as defects 102 and 104 in FIG. 1) and longitudinal rail defects (e.g., defects oriented predominantly parallel to the rail's running direction, such as defect 106 in FIG. 1). FIG. 4B shows an example of a skewed arrangement using a rectangular focus or a circular focus in combination with a plurality of receivers (e.g., arrays)—that can be either air-coupled transducers or ultrasonic wheel transducers—in a mono-directional inspection. FIG. 4C shows another example using a rectangular focus or a circular focus in combination with a plurality of receivers (e.g., arrays)—that can be either air-coupled transducers or ultrasonic wheel transducers—in a bi-directional inspection.

In either the mono-directional inspection of FIG. 4B or the bi-directional inspection of FIG. 4C, the processing of the received signals to detect defects in the rail can be done deterministically or statistically through one of an outlier analysis, an anomaly detection, or a discordancy test. To reiterate, in the bi-directional inspection of FIG. 4C, the comparison is made between the signals measured by the two receiver arrays 600 and 601, and any difference in signal amplitude, energy, phase, velocity or the like can be used to detect the presence of a defect in rail 105 between the two receiver arrays.

Figure 5:
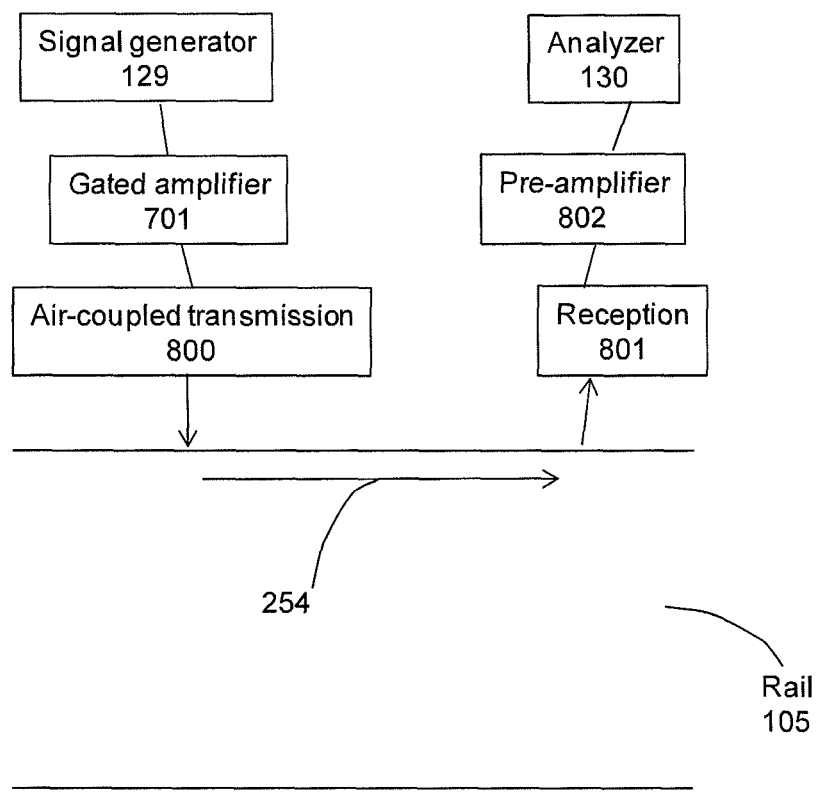
FIG. 5 depicts an example of a system for performing air-coupled guided wave testing of rails.

As shown in FIG. 5, in some implementations, the signal generator 129 may generate a narrowband tone burst voltage to excite the air-coupled transmitter 800. A gated amplifier 701 may be implemented between the signal generator 129 and the air-coupled transmitter 800 to boost the ultrasonic signal generated by the transmitter into air. For example, the gated amplifed may be configured to output a tone burst signal of 800 Volts peak-to-peak amplitude for five sinusoidal cycles to the transmitter, although other voltage values or other numbers of sinusoidal cycles can be used as well. By using the tone burst at a controlled frequency, a guided wave 254 of controlled mode and frequency content is excited into rail 105, and the wave may be sensitive to certain internal defects.

On the receiving side, as also shown in FIG. 5, a preamplifier 802 may be used to increase the signal measured by the air-coupled receivers or ultrasonic wheel receivers 801. Also, in some implementations, the analyzer 130 may include matched filters. The matched filtering of the signals detected by the air-coupled receivers or ultrasonic wheel receivers 801 may be based on a reference (or predetermined) tone burst signal sent to the air-coupled transmitter 800. The matched filtering may increase the signal-to-noise ratio of the measurements.

In another implementation of FIG. 5, a "chirped" signal can be used, instead of a tone burst signal, to excite the transmitter 800. On the receiving side, the matched filtering in this case may be done with the "chirped" excitation signal to increase the signal-to-noise ratio of the measurements.

The scheme shown in FIG. 5 can also be used in the bi-directional mode of testing where at least two receivers are positioned on opposite sides of the transmitter following FIGS. 2B and 3B.

In some implementations, the analyzer 130 may statistically process the received signals to improve the detectability of defects and minimize false positives. In statistical mode, analyzer 130 compares the received signals at one or more inspection positions to expected signal values, such as historical or baseline data. For example, historical data may comprise statistical parameters of signals previously collected at several positions along a certain length of rail, such as a so-called "benchmark" or "baseline" rail. The historical data may also include past measurements of the same rail (or rail type) under test. The historical data may also include averages, standard deviations, and the like of signals previously collected over rails. The analyzer 130 may compare the received signals to the expected signal values based on statistical techniques, such as an outlier analysis, anomaly detection, discordancy test or other signal detection techniques, to detect whether the statistics of the received signals indicate the likelihood of a defect in the rail. The statistical comparison may be done in a univariate manner (e.g., using a single feature, such as peak amplitude, of the received signals) or in a multivariate manner (e.g., using multiple features, such as a peak amplitude, a root mean square, a variance, statistical moments and the like, of the received signals).

The generators described herein may be implemented as a device for applying energy to the rail under test. The energy applied may be in the form of acoustic wave energy (e.g., where a piezoelectric ultrasonic transducer that emits ultrasonic waves is used). In any case, the applied energy causes waves in the ultrasonic portion of the spectrum to propagate through rail as ultrasonic guided waves. In some implementations where the dimensions of the rail are such that multiple measurements are required (e.g., for a long rail of a railroad track that may be extending over hundreds or thousands of miles), the generator may be mounted or fitted on a moving structure (for example, a carriage towed, or pushed, by a locomotive). Under those circumstances, the generator applies energy to the rail along a moving application point. The moving application point may be moving at a speed matching, for example, the speed of the locomotive or slower.

In some implementations, the detector may be configured to detect particular types of waves by controlling, for example, a time window during which the detector detects traveling waves. For example, certain waves may reach the surface near which the detector is located during some estimated time period, while other types of waves may reach the detector at other estimated time periods. Thus, by detecting traveling waves at pre-determined time periods, the detector may be configured to detect particular waves, such as ultrasonic guided waves, that traveled over some estimated path. Moreover, the detector may, in some implementations, include a processor to determine a transform, such as for example a Fourier Transform/Fast Fourier Transform, of the signals from the generator. These transformed signals may be provided to the analyzer 130 to detect defects.

Figure 6:
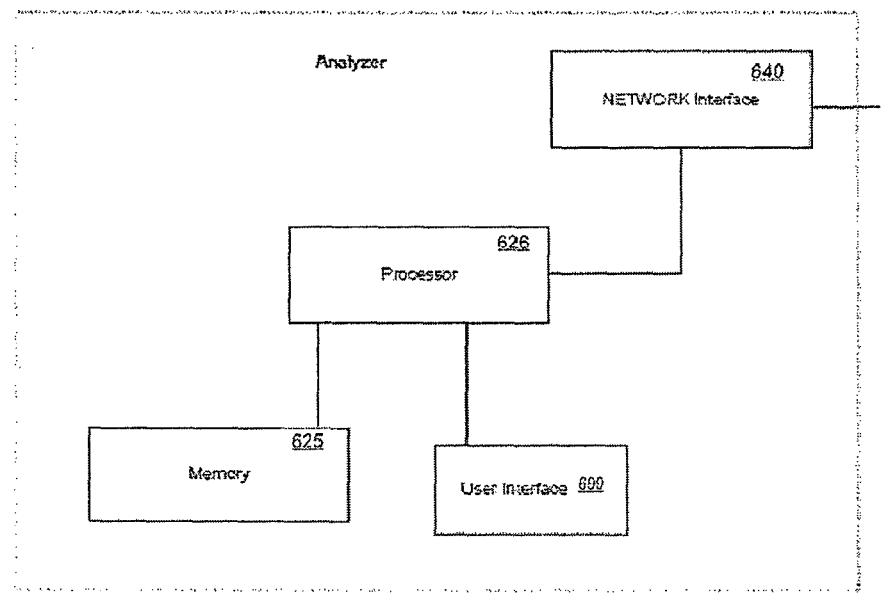
FIG. 6 depicts an example of an analyzer used in connection with detecting defects in rail.

In some implementations, the analyzer 130 may be implemented as processor-based systems that include at least one processor and at least one memory. FIG. 6 depicts an example implementation of an analyzer 800. The analyzer 800 may include one or more of network interfaces, such as for example network interface 640 for coupling to wired and/or wireless networks, at least one processor, such as for example a processor 626 for executing program code stored in memory 625. Furthermore, the program code may include instructions to perform one or more of process described herein including one or more aspects of the process. The analyzer 800 may also include a user interface 699 to allow a user to interact with analyzer 800.

The systems and methods disclosed herein may be embodied in various forms including, for example, a data processor, such as for example a computer that also includes a storage, digital electronic circuitry, firmware, software, or in combinations of them. Moreover, the above-noted features and other aspects and principles of the present disclosed embodiments may be implemented in various environments. Such environments and related applications may be specially constructed for performing the various processes and operations according to the disclosed embodiments or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the disclosed embodiments, or it may be more convenient to construct a specialized apparatus or system to perform the required methods and techniques.

The systems and methods disclosed herein may be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

The foregoing description is intended to illustrate but not to limit the scope of the invention, which is defined by the scope of the appended claims. Other embodiments are within the scope of the following claims.

What is claimed:

1. A method comprising
generating, by an air-coupled transducer, a first ultrasonic guided wave to cause the generated ultrasonic guided wave to propagate from a first side of a rail being tested for one or more defects, the rail defining a first axis in a direction of the rail, the rail further defining a second axis perpendicular to the first axis;
controlling, by a controller, a frequency of the first ultrasonic guided wave based on at least changing the frequency of a voltage sent to the air-coupled transducer;
receiving, by a receiver, a second ultrasonic guided wave from a second side of the rail, the second ultrasonic guided wave based on at least the first ultrasonic guided wave, the first side of the rail being opposite the second side of the rail along the second axis, and the receiver being positioned apart from the air-coupled transducer at an offset from the second axis at an angle; and
analyzing a signal representative of the received second ultrasonic guided wave to detect the one or more defects in the rail.

2. The method of claim 1, wherein changing the frequency of the voltage sent to the air-coupled transducer comprises generating a narrowband tone burst voltage to excite the air-coupled transducer for generating the first ultrasonic guided wave.

3. The method of claim 1, further comprising:
receiving, by a second receiver, a third ultrasonic guided wave from the second side of the rail, the third ultrasonic guided wave based on at least the first ultrasonic guided wave, the second receiver being positioned apart from the air-coupled transducer at a second offset from the second axis at a second angle, the second receiver being positioned apart from the receiver along the first axis; and
analyzing a signal representative of the received third ultrasonic guided wave based on at least a comparison against the signal representative of the received second ultrasonic guided wave to detect the one or more defects in the rail.

4. The method of claim 1, wherein the receiver comprises at least one wheel containing at least one transducer configured to receive the second ultrasonic guided wave.

5. The method of claim 1, further comprising:
receiving, at a first plurality of receivers comprising the receiver, a plurality of first waves based on at least the first ultrasonic guided wave, the first plurality of receivers being positioned apart from the air-coupled transducer at first offset angles below the second axis, the plurality of first waves comprising the second ultrasonic guided wave;
receiving, at a second plurality of receivers, a plurality of second waves based on at least the first ultrasonic guided wave, the second plurality of receivers being positioned apart from the air-coupled transducer at second offset angles below the second axis; and
analyzing signals representative of the plurality of first and second waves to detect the one or more defects in the rail.

6. The method of claim 1, wherein the generated first ultrasonic guided wave comprises at least one of a rectangular shape or a circular shape, when measured at a surface of the rail.

7. The method of claim 6, wherein the at least one of the rectangular shape or the circular shape is at least one of focused or unfocused with respect to the surface of the rail.

8. The method of claim 1, wherein the air-coupled transducer includes one or more of a piezoelectric crystal, a piezo-composite crystal, or a capacitive device.

9. The method of claim 1, wherein the analyzing comprises:
comparing the signal representative of the second ultrasonic guided wave to a reference signal; and
determining, based on the comparing, whether a defect parallel to the first axis is present in the rail.

10. The method of claim 1, wherein the analyzing comprises:
processing the signal representative of the second ultrasonic guided wave based on matched filtering, wherein the matched filtering is based on an excitation signal of a controlled frequency.

11. The method of claim 1, wherein the analyzing comprises:
processing the signal representative of the second ultrasonic guided wave, wherein the processing includes comparing a current measurement of the rail to a set of historical reference measurements of the rail based on at least one of:
an outlier analysis,
an anomaly detection, and
a discordancy test.

12. An apparatus comprising:
an air-coupled ultrasonic transducer configured to at least generate a first ultrasonic guided wave, the air-coupled transducer further configured to cause the generated ultrasonic guided wave to propagate from a first side of a rail being tested for one or more defects, the rail defining a first axis in a direction of the rail, the rail further defining a second axis perpendicular to the first axis;
a controller configured to at least control the frequency of the first ultrasonic guided wave based on at least changing a frequency of a voltage sent to the air-coupled transducer;
a receiver configured to at least receive a second ultrasonic guided wave, the second ultrasonic guided wave received from a second side of the rail, the second ultrasonic guided wave based on at least the first ultrasonic guided wave, the first side of the rail being opposite the second side of the rail along the second axis, and the receiver being positioned apart from the air-coupled transducer at an offset from the second axis at an angle; and
a processor configured to at least analyze a signal representative of the received second ultrasonic guided wave to detect the one or more defects in the rail.

13. The apparatus of claim 12, wherein the controller is further configured to at least change the frequency of the voltage sent to the air-coupled transducer based on at least generating a narrowband tone burst voltage to excite the air-coupled transducer for generating the first ultrasonic guided wave.

14. The apparatus of claim 12, further comprising:
a second receiver configured to at least receive a third ultrasonic guided wave from the second side of the rail, the third ultrasonic guided wave based on at least the first ultrasonic guided wave, the second receiver being positioned apart from the air-coupled transducer at an offset from the second axis at a second angle, the second receiver being positioned apart from the receiver along the first axis, wherein the processor is further configured to at least analyze a signal representative of the received third ultrasonic guided wave based on at least a comparison against the signal representative of the received second ultrasonic guided wave to detect the one or more defects in the rail.

15. The apparatus of claim 12, wherein the receiver comprises at least one wheel containing at least one transducer configured to receive the second ultrasonic guided wave.

16. The apparatus of claim 12, further comprising:

a first plurality of receivers comprising the receiver, the first plurality of receivers being positioned apart from the air-coupled transducer at first offset angles below the second axis, the first plurality of receivers configured to receive a plurality of first waves based on at least the first ultrasonic guided wave, the plurality of first waves comprising the second ultrasonic guided wave; and a second plurality of receivers, the second plurality of receivers being positioned apart from the air-coupled transducer at second offset angles above the second axis, the second plurality of receivers configured to receive a plurality of second waves based on at least the first ultrasonic guided wave, wherein the processor is further configured to at least analyze signals representative of the plurality of first and second waves to detect the one or more defects in the rail.

17. The apparatus of claim 16, wherein the generated first ultrasonic guided wave comprises at least one of a rectangular shape or a circular shape, when measured at a surface of the rail.

18. The apparatus of claim 17, wherein the at least one of the rectangular shape or the circular shape is at least one of focused or unfocused with respect to the surface of the rail.

19. The apparatus of claim 12, wherein the air-coupled transducer includes one or more of a piezoelectric crystal, a piezo-composite crystal, or a capacitive device.

20. The apparatus of claim 12, wherein the processor is further configured to compare the signal representative of the second ultrasonic guided wave to a reference signal and determine, based on the comparison, whether a defect parallel to the first axis is present in the rail.

* * * * *